United States Patent

Ryback et al.

(10) Patent No.: US 6,605,273 B2
(45) Date of Patent: Aug. 12, 2003

(54) RENAL CELL CARCINOMA TREATMENT

(75) Inventors: Mary Ellen Ryback, Waren, NJ (US); Esther Helen Rose, Westfield, NJ (US)

(73) Assignee: Schering Corporation, Kenilworth, NJ (US)

(*) Notice: Subject to any disclaimer, the term of this patent is extended or adjusted under 35 U.S.C. 154(b) by 0 days.

(21) Appl. No.: 09/901,522

(22) Filed: Jul. 9, 2001

(65) Prior Publication Data

US 2001/0053548 A1 Dec. 20, 2001

Related U.S. Application Data

(63) Continuation of application No. 09/544,232, filed on Apr. 7, 2000, now abandoned.
(60) Provisional application No. 60/128,295, filed on Apr. 8, 1999.

(51) Int. Cl.[7] ................. A61K 38/21; A61K 45/00; A61K 38/00; C07K 17/00; A23J 1/00

(52) U.S. Cl. ................. 424/85.7; 424/85.1; 424/85.4; 530/351; 530/421; 514/2

(58) Field of Search ................ 514/2; 530/351, 530/421; 424/85.7, 85.1, 85.4

(56) References Cited

U.S. PATENT DOCUMENTS

| | | | |
|---|---|---|---|
| 4,492,537 A | 1/1985 | Awerkamp | 417/404 |
| 4,530,901 A | 7/1985 | Weissmann | 435/70 |
| 4,695,623 A | 9/1987 | Stabinsky | 530/351 |
| 4,766,106 A | 8/1988 | Katre et al. | 514/12 |
| 4,897,471 A | 1/1990 | Stabinsky | 536/27 |
| 4,917,888 A | 4/1990 | Katre et al. | 424/85.91 |
| 5,382,427 A | 1/1995 | Plunkett et al. | 424/85.2 |
| 5,711,944 A | 1/1998 | Gilbert et al. | 424/85.7 |
| 5,762,923 A | 6/1998 | Gross et al. | 424/85.7 |
| 5,766,582 A | 6/1998 | Yuen et al. | 424/85.7 |
| 5,766,897 A | 6/1998 | Braxton | 435/172.1 |
| 5,776,897 A | 7/1998 | Lewis et al. | 514/12 |
| 5,908,621 A | 6/1999 | Glue et al. | 424/85.7 |
| 5,951,974 A | 9/1999 | Gilbert et al. | 424/85.7 |
| 5,985,263 A | 11/1999 | Lee et al. | 424/85.2 |
| 6,362,162 B1 | 3/2002 | Rybak et al. | 514/2 |
| 2001/0038833 A1 | 11/2001 | Rybak et al. | 424/85.7 |

FOREIGN PATENT DOCUMENTS

| | | |
|---|---|---|
| EP | 0 510 356 A1 | 10/1992 |
| EP | 0 593 868 A1 | 4/1994 |
| EP | 0 236 987 B1 | 12/1994 |
| EP | 0 809 996 A2 | 12/1997 |
| WO | WO 95/13090 | 5/1995 |
| WO | WO 98/48840 * | 11/1998 |
| WO | WO 99/48535 | 9/1999 |

OTHER PUBLICATIONS

Hasford et al. "Interferon–α and Hydroxyurea in Early Chronic Myeloid Leukemia: A Comparative Analysis of the Italian and German Chronic Myeloid Leukemia Trials with Interferon–α," Blood 87 (12)5384–5391 (1996).

Ozer et al., "Prolonged Subcutaneous Administration of Recombinant α2b Interferon in Patients with Previously Untreated Philadelphia Chromosome–Positive Chronic–Phase Chronic Myelogenous Leukemia: Effect on Remission Duration and Survival: Cancer and Leukemia Group B Study 8583," Blood 82:10 pp. 2975–2984, Nov. 15, 1993.

Atzpodien et al., "Home therapy with recombinant interleukin–1 and interferon–α2b in advanced human malignancies," The Lancet, 335, pp. 1509–1512 (1990).

Cascinelli et al., "Results of adjuvant interferon study in WHO melanoma programme," The Lancet, 343:913–914, Apr. 9, 1994.

Déprés–Brummer et al., "A Phase II Study of Ambulatory Chronomodulated High Dose Interferon (IFNα2a) Against Metastatic Renal Cancer (MRC)," American Society of Clinical Oncology, Abstract No. 628, 15:248, Mar. 1996.

Escudier et al., "The FNCLCC Crecy Trial: Interleukin 2 (IL2) + Interferon (IFN) is the Optimal Treatment to Induce Response in Metastatic Renal Cell Carcinoma (MRCC)," American Society of Clinical Oncology, Abstract No. 629, 15:248, Mar. 1996.

Gitlitz et al., "Fluoropyrimidines Plus Interleukin–2 and Interferon–α in the Treatment of Metastatic Renal Cell Carcinoma: The UCLA Kidney Cancer Program," American Society of Clinical Oncology, Abstract No. 630, 15:248, Mar. 1996.

Kantarjian et al., "Treatment of Chronic Myelogenous Leukemia: Current Status and Investigational Options," Blood 87:8 pp. 3069–3081, Apr. 15, 1996.

Hehlman et al., "Randomized Comparison of Interferon–α With Busulfan and Hydroxyurea in Chromic Myelogenous Leukemia," Blood 84:12 pp. 4064–4077, Dec. 15, 1994.

Kantarjian et al., "Chronic Myelogenous Leukemia: A Concise Update," Blood 82:3 pp. 691–703, Aug. 1, 1993.

Nicolaou et al., "Total Synthesis of Taxol. 1. Retrosynthesis, Degradation, and Reconstitution," J. Am. Chem. Soc. 117 pp. 624–633, 1995.

Hasford, et al "Interferon–α and Hydroxyurea in Early Chronic Myeloid Leukemia: A Comparative Analysis of the Italian and German Chronic Myeloid Leukemia Trials With Interferon–α,".

(List continued on next page.)

Primary Examiner—Yvonne Eyler
Assistant Examiner—Janet L. Andres

(57) ABSTRACT

Methods for treating treatment-naive as well as treatment-experienced patients having RCC to achieve at least a partial tumor response involving administering a therapeutically effective amount of pegylated interferon-alpha, e.g., pegylated interferon alpha-2b as monotherapy or in association with a therapeutically effective amount of IL-2 are disclosed.

20 Claims, No Drawings

OTHER PUBLICATIONS

Ozer et al., "Prolonged Subcutaneous Administration of Recombinant α2b Interferon in Patients with Previously Untreated Philadelphia Chromosome–Positive Chronic–Phase Chronic Myelogenous Leukemia: Effect on Remission Duration and Survival: Cancer and Leukemia Group B Study 8583," Blooc 82:10 pp. 2975–2984, Nov. 15, 1993.

Ohnishi et al., "A Randomized Trial Comparing Interferon–α With Busulfan for Newly Diagnosed Chronic Myelogenous Leukemia in Chronic Phase," Blood 86:3 pp. 906–916, Aug. 1, 1995.

Creagon et al., "Randomized, Surgical Adjuvant Clinical Trial of Recombinant Interferon Alfa–2a in Selected Patients With Malignant Melanoma," Journal of Clinical Oncology, 13:13 pp. 2776–2783 Nov. 1995.

Bergmann et al., "Daily Alternating Administrationn of High–Dose Alph–2b–Interferon and Interleukin–2 Bolus Infusion in Metastatic Renal Cell Cancer," Cancer 72:5, pp. 1735–1742 Sep. 1, 1993.

Umeda et al., "Phase II Study of Alpha Interferon on Renal Cell Carcinoma," Cancer 58:1231–1235, Sep. 15, 1986.

Sokal et al., "Preferentiall Inhibition by Cytarabine of CFU–GM From Patients With Chronic Granulocytic Leukemia," Cancer 59:197–202, Jan. 1, 1987.

Fleming et al., "One–Sample Multiplel Testing Procedure for Phase II Clinical Trials," Biometrics 38:143–151 Mar. 1982.

Rosenberg, et al., "Experience with the Use of High–Dose Interleukin–2 in the Treatment of 652 Cancer Patients," Ann. Surg. 210:4 pp. 475–485.

Kantarjian et al., "Prolonged Survical in Chronic Myelogenouos Leukemia after Cytogenetic Response to Interferon–α Therpay," Ann Intern Med. 122:254–261, 1995.

Talphaz et al., "Interferon–Alpha Produces Sustained Cytogenetic Responses in Chronic Myelogenouos Leukemia," Annals of Internal Medicine, 114:7 Apr. 1, 1991.

Négrier et al., "Intensive Regimen of Cytokines with Interleukin–2 and Interferon Alfa–2B in Selected Patients with Metastatic Renal Carcinoma," Journal of Immunotherapy, 17:62–68 1995.

Goldman, "Optimizing Treatment for Chronic Myeloid Leukeemia," The New England Journal of Medicine, 337:4, pp. 270–271, Jul. 24, 1997.

Guilhot, et al., "Interferon Alfa–2b Combined with Cytarabine Versus Interferon Alone in Chronic Myelogenous Leukemia," The New England Journal of Medicine, 337:4 pp. 223–229.

The Italian Cooperative Study Group on Chronic Myeloid Leukemia, "Interferon Alfa–2a as Compared with Conventional Chemotherapy for the Treatment of Chronic Myeloid Leukemia," The New England Journal of Medicine, 330:12 pp. 820–825, Mar. 24, 1994.

Atzpodien et al., "Multiinstitutional Home–Therapy Trial of Recombinant Human Interleukin–2 and Interferon Alfa–2 in Progessive Metastatic Renal Cell Carcinoma," Journal of Clinical Oncology, 13:2 pp. 497–501 Feb. 1995.

Kirkwood et al., "Interferon Alfa–2b Adjuvant Therapy of High–Rish Resected Cutaneous Melanoma: The Eastern Cooperative Oncology Group Trial EST 1684," Journal of Clinical Oncology, 14: 1 pp. 7–17, Jan. 1996.

Atzpodien et al., "Home therapy with recombinant interleukin–2 and interferon–α2b in advanced human malignancies," The Lancet, 335 pp. 1509–1512.

Alfonso Gennaro, "Antineoplastic and Immunoactive Drugs," Remington's $18^{th}$ Ed., 1990.

Bukowski, "Phase 1 Study of Polyethylene Glycol (PEG) Interferon Alpha–2B (PEG INTRON) in Patients with Solid Tumors," American Society of Clinical Oncology, 1999 Abstract.

Carlsson, et al., "Results of adjuvant interferon study in WHO melanoma programme," The Lancet, 343:913–914 Apr. 9, 1994.

American Society of Clinical Oncology 15:May 1996.

P. Sagaster et al., "Randomised Study Using IFN–α versus IFN–α plus coumarin and cimetidine for treatment of advanced renal cell cancer," Annals of Oncology 6:999–1003, 1995.

D. Osoba, et al., "Modification of the EORTC QLQ–C30 (version 2.0) based on content validity and reliability testing in large samples of patients with cancer," quality of Life Research 6:103–108, 1997.

Sewa S. Legha, "The Role of Interferon Alfa in the Treatment of Metastatic Melanoma," Seminars in Oncology, 24:1 Suppl 4 (Feb.) 1997, pp. S4–24–54–31.

W. Levens et al., "Long–Term Interferon Treatment in Metastatic Renal Cell Carcinoma," Eur Urol. 16:378–381, 1989.

Janice P. Dutcher, et al., "Outpatient Subcutaneous Interleukin–2 and Interferon–Alpha for Metastatic Renal Cell Cancer: Five–Year Follow–up of the Cytokine Working Group Study," The Cancer Journal from Scientific American 3:3 May/Jun. 1997.

Talpaz et al, "Phase I Study of Polyethylene Glycol (PEG) Interferon Alpha–2B (Intron–A) in CML Patients,", Blood, vol. 92, Issue 10, Suppl. 1 part 1–2, Nov. 15, 1998, pp. 251A.

Talpaz et al, "Phase I Study Of Pegylated–Interferon α–2A (PEGASYS™) In Patients With Chronic Myelogenous Leukemia (CML)", Blood, vol. 94, Issue 10, Suppl. 1, part 1, Nov. 15, 1999, pp. 530A.

Walther, P.J. et al., "Treatment of Metastatic Renal Cell Carcinoma (RCC) with Continuous Infusion 5–Fluorouracil and Interferon Alpha–2A in the Home Setting: A Phase I–II Trial", Proceedings of the American Urological Association, vol. 155, May 1996 Supplement, p. 388A.

Gebrosky et al., "Treatment of Renal Cell Carcinoma with 5–Fluorouracil and Alfa–Interferon", Urology 50(6) 1997, 863–868.

Atzpodien J. et al., "Interleukin–2 in Combination with Interferon–α and 5–Fluorouracil Metastatic Renal Cell Cancer", European Journal of Cancer, vol. 29A, Suppl. 5, 1993, pp. S6–S8.

* cited by examiner

RENAL CELL CARCINOMA TREATMENT

CROSS-REFERENCE TO RELATED APPLICATIONS

This application is a continuation of copending U.S. Ser. No. 09/544,232 filed Apr. 7, 2000 (now abandoned) which is a non-provisional application that claims the priority of provisional U.S. Ser. No. 60/128,295 filed Apr. 8, 1999. The Applicants' claim the benefits of these applications under 35 U.S.C. §§119(e) and 120.

Throughout this disclosure, various publications, patents and patent applications are referenced. The disclosures of these publications, patents and patent applications are herein incorporated by reference.

BACKGROUND OF THE INVENTION

This invention relates to an improved therapy for treating patients having renal cell carcinoma ("RCC") by administering a therapeutically effective dose of pegylated interferon-alpha for a time sufficient to achieve at least a partial tumor response.

Metastatic renal cell carcinomas are generally resistant to chemotherapy, either with single agents or in combination. Greater success has been seen with immunotherapy, particularly with the use of interleukin-2 ("IL-2"). Therapy with high dose intravenous IL-2 has resulted in objective tumor responses in approximately 14% of patients, some with long durability. The administration of high dose IL-2 is associated with capillary leak syndrome, which results in hypotension and reduced organ perfusion which can be severe and sometimes fatal. These toxicities have generally inhibited the use of IL-2 to a highly selected group of patients administered by physicians with significant experienced in its administration. The use of lower-dose and subcutaneously (SC) administered regimens of IL-2 alone or in combination with other biologic agents, including interferon-α, has been explored in an effort to develop a more broadly applicable therapy for this disease. For example, Atzpodien, J., et al. disclosed in J. Clin Oncol., 1995, Volume 13, pages 497–501 that the combination treatment of subcutaneous ("SC") administration and lower dose regimens of interferon alpha-2b and SC interleukin-2 to patients with progressive metastatic RCC produced tumor response with lower toxicity. It must be noted that the response rates are low and that injections of interferon alpha-2b 5 million IU/m$^2$ three times a week ("TIW"), were required to achieve these results. In addition, interferon alpha-2b has many side effects that a substantial number of patients find unacceptable, and patient compliance with the TIW injections of interferon alpha-2b has become a problem. Accordingly, there is a need for an improved therapy for treating patients having RCC.

SUMMARY OF THE INVENTION

The present invention provides a method of treating a patient having renal cell carcinoma which comprises administering to such a patient a therapeutically effective dose of pegylated interferon alpha for a time period sufficient to effect at least a partial tumor response.

The present invention also provides a method of treating a patient having metastatic renal cell carcinoma which comprises administering to said patient an effective amount of pegylated interferon-alpha once a week for a time period sufficient to effect at least a partial tumor response.

The present invention further provides a method of treating a patient having metastatic renal cell carcinoma which comprises administering to such a patient about 4.5 micrograms/kg to about 9.0 micrograms/kg of pegylated interferon alpha-2b once a week for a time period sufficient to effect at least a partial tumor response.

DETAILED DESCRIPTION OF THE INVENTION

The present invention provides an improved method of treating patients with RCC—especially those with metastatic RCC. The improved method provides a safer and more efficacious and tolerable treatment for RCC by use of weekly injections of pegylated interferon alpha alone or in combination with immunotherapeutic agents such as IL-2 or fluorouracil (5-FU"). The RCC patients include those newly diagnosed with this disease as well as those patients intolerant or resistant to interferon alpha. Treatment with pegylated interferon alpha in accordance with the present invention will continue for a minimum of six months, and preferably for at least twelve months unless there is clinical evidence of disease progression, unacceptable toxicity or the patient requests that the therapy be discontinued.

When the pegylated interferon-alpha administered is a pegylated interferon alpha-2b, the therapeutically effective amount of pegylated interferon alpha-2b administered is in the range of about 4.5 to about 9.0 micrograms per kilogram of pegylated interferon alpha-2b administered once a week (QW), preferably in the range of about 4.5 to about 6.5 micrograms per kilogram of pegylated interferon alpha-2b QW, more preferably in the range of about 5.5 to about 6.5 micrograms per kilogram of pegylated interferon alpha-2b QW, and most preferably in the range of about 6.0 micrograms per kilogram of pegylated interferon alpha-2b administered QW.

When the pegylated interferon-alpha administered is a pegylated interferon alpha-2a, the therapeutically effective amount of pegylated interferon alpha-2a administered is in the range of about 50 micrograms to about 500 micrograms once a week ("QW"), preferably about 200 micrograms to about 250 micrograms QW.

The term "pegylated interferon alpha" as used herein means polyethylene glycol modified conjugates of interferon alpha, preferably interferon alpha-2a and -2b. The preferred polyethylene-glycol-interferon alpha-2b conjugate is PEG$_{12000}$-interferon alpha 2b. The phrases "12,000 molecular weight polyethylene glycol conjugated interferon alpha" and "PEG$_{12000}$-IFN alpha" as used herein mean conjugates such as are prepared according to the methods of International Application No. WO 95/13090 and containing urethane linkages between the interferon alpha-2a or -2b amino groups and polyethylene glycol having an average molecular weight of 12000.

The preferred PEG$_{12000}$-interferon alpha-2b is prepared by attaching a PEG polymer to the epsilon amino group of a lysine residue in the IFN alpha-2b molecule. A single PEG$_{12000}$ molecule is conjugated to free amino groups on an IFN alpha-2b molecule via a urethane linkage. This conjugate is characterized by the molecular weight of PEG$_{12000}$ attached. The PEG$_{12000}$-IFN alpha-2b conjugate is formulated as a lyophilized powder for injection. The objective of conjugation of IFN alpha with PEG is to improve the delivery of the protein by significantly prolonging its plasma half-life, and thereby provide protracted activity of IFN alpha.

The term "interferon-alpha" as used herein means the family of highly homologous species-specific proteins that inhibit viral replication and cellular proliferation and modulate immune response. Typical suitable interferon-alphas include, but are not limited to, recombinant interferon alpha-2b such as Intron-A interferon available from Schering Corporation, Kenilworth, N.J., recombinant interferon alpha-2a such as Roferon interferon available from Hoffmann-La Roche, Nutley, N.J., recombinant interferon alpha-2C such as Berofor alpha 2 interferon available from Boehringer Ingelheim Pharmaceutical, Inc., Ridgefield, Conn., interferon alpha-n1, a purified blend of natural alpha interferons such as Sumiferon available from Sumitomo, Japan or as Wellferon interferon alpha-n1 (INS) available from the Glaxo-Wellcome Ltd., London, Great Britain, or a consensus alpha interferon such as those described in U.S. Pat. Nos. 4,897,471 and 4,695,623 (especially Examples 7, 8 or 9 thereof) and the specific product available from Amgen, Inc., Newbury Park, Calif., or interferon alpha-n3 a mixture of natural alpha interferons made by Interferon Sciences and available from the Purdue Frederick Co., Norwalk, Conn., under the Alferon Tradename. The use of interferon alpha-2a or alpha-2b is preferred. Since interferon alpha-2b, among all interferons, has the broadest approval throughout the world for treating chronic hepatitis C infection, it is most preferred. The manufacture of interferon alpha-2b is described in U.S. Pat. No. 4,530,901.

Other interferon alpha conjugates can be prepared by coupling an interferon alpha to a water-soluble polymer. A non-limiting list of such polymers include other polyalkylene oxide homopolymers such as polypropylene glycols, polyoxyethylenated polyols, copolymers thereof and block copolymers thereof. As an alternative to polyalkylene oxide-based polymers, effectively non-antigenic materials such as dextran, polyvinylpyrrolidones, polyacrylamides, polyvinyl alcohols, carbohydrate-based polymers and the like can be used. Such interferon alpha-polymer conjugates are described in U.S. Pat. Nos. 4,766,106, 4,917,888, European Patent Application No. 0 236 987, European Patent Application Nos. 0 510 356, 0 593 868 and 0 809 996 (pegylated interferon alpha-2a) and International Publication No. WO 95/13090.

Pharmaceutical composition of pegylated interferon alpha-suitable for parenteral administration may be formulated with a suitable buffer, e.g., Tris-HCl, acetate or phosphate such as dibasic sodium phosphate/monobasic sodium phosphate buffer, and pharmaceutically acceptable excipients (e.g., sucrose), carriers (e.g. human serum albumin), toxicity agents (e.g. NaCl), preservatives (e.g. thimerosol, cresol or benylalcohol), and surfactants (e.g. tween or polysorabates) in sterile water for injection. The pegylated interferon alpha-may be stored as lyophilized powders under a refrigeration at 2°–8° C. The reconstituted aqueous solutions are stable when stored between 2° and 8° C. and used within 24 hours of reconstitution. See for example U.S. Pat. Nos., 4,492,537; 5,762,923 and 5,766,582. The reconstituted aqueous solutions may also be stored in prefilled, multi-dose syringes such as those useful for delivery of drugs such as insulin. Typical suitable syringes include systems comprising a prefilled vial attached to a pen-type syringe such as the NOVOLET Novo Pen available from Novo Nordisk, as well as prefilled, pen-type syringes which allow easy self-injection by the user. Other syringe systems include a pen-type syringe comprising a glass cartridge containing a diluent and lyophilized pegylated interferon alpha powder in a separate compartment.

The term "tumor response" as used herein means a reduction or elimination of all measurable lesions.

The criteria for tumor response are based on the WHO Reporting Criteria [WHO Offset Publication, 48-World Health Organization, Geneva, Switzerland, (1979)]. Ideally, all uni- or bidimensionally measurable lesions should be measured at each assessment. When multiple lesions are present in any organ, such measurements may not be possible and, under such circumstances, up to 6 representative lesions should be selected, if available.

The term "complete response ("CR")" as used herein means a complete disappearance of all clinically detectable malignant disease, determined by 2 observations not less than 4 weeks apart. A preliminary assessment may be made with two measurements.

The term "partial response" ("PR") as used herein in reference to (a) bidimensionally measurable disease means decrease by at least about 50% of the sum of the products of the largest perpendicular diameters of all measurable lesions as determined by 2 observations not less than 4 weeks apart and (b) unidimensionally measurable disease means decrease by at least about 50% in the sum of the largest diameters of all lesions as determined by 2 observations not less than 4 weeks apart. It is not necessary for all lesions to have regressed to qualify for partial response, but no lesion should have progressed and no new lesion should appear. Serial evidence of appreciable change documented by copies of radiographic studies must be obtained and must be available for subsequent review. The assessment should be objective.

The term "stable disease" ("SD") as used herein in reference to (a) bidimensionally measurable disease means less than about 50% decrease or less than about 25% increase in the sum of the products of the largest perpendicular diameters of all measurable lesions and (b) unidimensionally measurable disease, means less than about 50% decrease or less than about 25% increase in the sum of the diameters of all lesions. No new lesions should appear.

The term "progressive disease" ("PD") as used herein means a greater than or equal to about a 25% increase in the size of at least one bidimensionally (product of the largest perpendicular diameters) or unidimensionally measurable lesion or appearance of a new lesion. The occurrence of pleural effusion or ascites is also considered as progressive disease if this is substantiated by positive cytology. Pathological fracture or collapse of bone are not necessarily evidence of disease progression.

Overall Subject Tumor Response

Determination of overall subject tumor response for uni- and bidimensionally meaurable disease will be done according to the following table:

| Overall Subject Tumor Response | | |
|---|---|---|
| Response in Bidimensionally Measurable Disease | Response in Unidimensionally Measurable Disease | Overall Subject Tumor Response |
| PD | Any | PD |
| Any | PD | PD |
| SD | SD or PR | SD |
| SD | CR | PR |
| PR | SD or PR or CR | PR |
| CR | SD or PR | PR |
| CR | CR | CR |

PD: Progressive Disease.
CR: Complete Response.
PR: Partial Response.
SD: Stable Disease Evaluation of Response in the Presence of Non-Measurable Disease Non-measurable disease will not be used in the assessment of overall subject tumor response except in the following situations:
a) Overall complete response: if non-measurable disease is present, it should disappear completely. Otherwise, the subject cannot be considered as an "overall complete responder".
b) Overall progression: in case of a significant increase in the size of non-measurable disease or the appearance of a new lesion, the overall response will be progression.

The term "patients having renal cell carcinoma or "RCC" as used herein means any patient having RCC and includes treatment-naive patients as well as treatment-experienced patients as well as patients in the metastatic stage of RCC.

The term "treatment-naive patients" as used herein means patients with RCC—including newly-diagnosed RCC patients—who have never been treated with radiation therapy or any chemotherapy, e.g., fluorouracil ("5-FU") or hormonal therapy or immunotherapy, e.g. IL-2, as well as any interferon, including but not limited to interferon alpha, or pegylated interferon alpha.

The term "treatment-experienced patients" as used herein means those patients who have initiated some form of radiation therapy or hormonal therapy or chemotherapy including, but not limited to 5 FU, or immunotherapy including, but not limited to IL-2. Interleukin-2 is available under the PROLEUKIN® tradename from Chiron Corporation, Emeryville, Calif. 94608-3997. Fluorouracil or 5-FU is available as an injectable solution under the ADRUCIL® tradename from Pharmacia & Upjohn Co., Bridgewater, N.J. 08807-12665

The effective amount of IL-2 when used is in the range of about 5 to about 20 million international units ("IU") per square meter of body surface area ($m^2$) three times per week ("TIW") administered subcutaneously. In a preferred embodiment of the method of the present invention, the dosage and dosage regimen for SC administration of IL-2 in combination with pegylated interferon alpha will be about 20 million IU/$m^2$ TIW in the first week and every fourth week thereafter and about 5 million IU/$m^2$ TIW in the subsequent weeks of treatment, e.g., weeks 2, 3, 5, 6, 7, 9, 10, 11 et seq.

The effective amount of 5-FU when used is in the range of about 12 mg/kg/day IV (not to exceed 800 mg) for 5 days. If toxicity has not occurred, 6 mg/kg/day IV on days 7, 9, 11 and 13. For maintenance, mif toxicity to the first course was minal either repeat the course every 30 days or give 10 to 15 mg/kg (not to exceed 1 g) once a week, after recovery from the initial toxicity is complete. These doses may be reduced by the clinician depending upon the severity of the disease and the patient's condition and reaction to pegylated interferon alpha. A constant infusion with an implantable pump may be more effective and fewer toxic than periodic bolus injections.

Pegylated interferon-alpha formulations are not effective when administered orally, so the preferred method of administering the pegylated interferon-alpha is parenterally, preferably by subcutaneous, IV, or IM, injection. Of course, other types of administration of both medicaments, as they become available are contemplated, such as by nasal spray, transdermally, by suppository, by sustained release dosage form, and by pulmonary inhalation. Any form of administration will work so long as the proper dosages are delivered without destroying the active ingredient.

The following Clinical Study Design may be used to treat RCC patients in accordance with the method of the present invention. Many modifications of this Clinical Study Design protocol will be obvious to the skilled clinician, and the following Study Design should not be interpreted as limiting the scope of the method of this invention which is defined by the claims listed hereinafter Clinical Study Design In a preferred embodiment of the treatment method of the present invention, subjects with metastatic RCC will receive pegylated interferon alpha 2b, i.e., $PEG_{12000}$-interferon alpha 2b at doses of 6.0 micrograms per kilogram by subcutaneous injection once a week.

Duration of Study and Visit Schedule

The duration of this study is based upon achieveing a therapeutic response, and will be determined for each subject individually.

Treatment with PEG Intron will continue for a minimum of 6 months unless there is evidence of disease progression, unacceptable toxicity, or the subject requests that therapy be discontinued. Tumor response will be assessed beginning at week 8 will be evaluated every 8 weeks thereafter during the first year of study treatment. Population pharmacokinetics will be conducted at various timepoints throughout the study. In addition, quality of life and overall survival data will be collected. Subjects who achieve a complete or partial tumor response by 6 months will continue treatment for another 6 months.

The following clinical protocol may be used to administer the RCC therapy of the present invention:

The study population will include male and female patients with metastatic RCC and will be included if they meet the following inclusion and exclusion criteria:

Subject Inclusion Criteria

A subject is eligible to participate in this study if he or she:
a) has histologically documented metastic renal cell carcinoma.
b) has an ECOG Performance Status of 0 or 1.
c) is $\geq 18$ and $\leq 70$ years of age.
d) has a life expectancy of >8 weeks.
e) has adequate end organ function (hepatic, renal, bone marrow, cardiac) as indicated by laboratory values below:
  1) Hematology:
     Absolute neutrophil count (ANC) $\geq 3,000$ cells/$\mu L$.
     Platelet count $\geq 100,000$ cells/$\mu L$.
     Hemoglobin concentration $\geq 9$ g/dL.
  2) Renal and hepatic function:
     Serum creatinine $\leq 1.8$ mg/dL or calculated creatinine clearance of $\geq 50$ mL/minute.
     Serum bilirubin $\leq 1.25$ times the upper limit of normal (ULN), unless due to infiltration by disease.
     AST/ALT (SGOT/SGPT) $\leq 1.25$ times ULN, unless due to infiltration by disease.
     Negative HBs Ag.
  3) Normal plasma calcium.
f) has submitted a written voluntary informed consent before study entry, is willing to participate in this study and will complete all follow up assessments.

Subject Exclusion Criteria

A subject is not eligible to participate in this study if he or she:
a) has received any prior non-surgical treatment for RCC, including chemotherapy, adjuvant chemotherapy, immunotherapy, radiation therapy or hormonal therapy.

b) has evidence of CNS metastases.
c) has a known hypersensitivity to interferon-α.
d) has severe cardiovascular disease i.e., arrhythmias requiring chronic treatment or congestive heart failure (NYHA classification III or IV)
e) has a history of a neurophychiatric disorder requiring hospitalization.
f) has a history of seizure disorder.
g) has thyroid dysfunction not responsive to therapy.
h) has uncontrolled diabetes mellitus.
i) has a life-threatening second active malignancy.
j) has an ongoing active infection requiring antibiotics.
k) requires chronic treatment with systemic corticosteroids.
l) has a history of seropositivity for HIV.
m) is pregnant, lactating or of child-bearing potential and not practicing an effective means of contraception.
n) has active hepatitis.
o) is known to be actively abusing alcohol or drugs.
p) has received any experimental therapy within 30 days of enrollment into this study and
q) has not recovered from the effects of any recent surgery.

Subject Discontinuation Criteria

It is the right and duty of the clinical investigator to interrupt the treatment of any subject whose health or well being may be threatened by continuation in this study.

A subject may be discontinued prior to completion of the study if he or she:
a) has a clinically significant adverse event as determined by the Principal Investigator.
b) requests to be withdrawn from the study.
c) is unable to complete the study evaluations/visits because of unforeseen circumstances.
d) develops other conditions for which, in the investigator's opinion, it is in the subject's best interest to be withdrawn from the study.
e) develops severe depression or any other psychiatric disorder requiring hospitalization.
f) experiences a serious allergic response to the study drug manifested by angioedema, bronchoconstriction or anaphylaxis.

Another Clinical Study Design

In another preferred embodiment of the treatment method of the present invention, subjects with metastatic RCC will receive pegylated interferon alpha 2b, i.e., $PEG_{12000}$-interferon alpha 2b at doses of 6.0 micrograms per kilogram by subcutaneous injection once a week in combination with SC administration of IL-2 in accordance with the following regimen: 20 million IU of IL-2/$M^2$ TIW in week 1 and every fourth week thereafter and 5 million IU of IL-2/$M^2$ TIW in weeks 2, 3, 5, 6, 7, 9, 10, 11 et seq.

Analysis of Primary and Secondary Endpoints

The primary efficacy endpoint will be the tumor response at 6 months. The primary analysis will be the comparison of treatment groups with respect to the proportion of subjects with major tumor response at 6 months using the Cochran Mantel-Haenszel test adjusting for strata. Odds ratio and 95% confidence intervals for the odds ratio will be summarized.

The secondary endpoints of the study will be relapse-free survival at 3, 6 and 12 months, and overall survival. Relapse-free survival and overall survival will be analyzed using the log-rank statistic. Kaplan-Meier estimates of the survival curves will be provided. Hazar ratio and 95% confidence interval for the hazard ratio will be obtained using Cox's proportional hazards model.

What is claimed is:

1. A method of treating a human patient having metastatic renal cell carcinoma which comprises administering to said patient 200 to 250 micrograms of pegylated interferon-alpha-2a once a week for a time period sufficient to effect at least a partial tumor response.

2. The method of claim 1 wherein the patient is a treatment-naive patient.

3. The method of claim 2 wherein the treatment-naive patient is one having newly diagnosed renal cell carcinoma.

4. The method of claim 1 wherein the patient is treatment-experienced patient.

5. The method of claim 4 wherein the treatment experienced patient is intolerant to interferon alpha or resistant to interferon alpha.

6. The method of claim 1 wherein the tumor response is a complete tumor response.

7. The method of claim 1 wherein the time period is at least 3 months.

8. The method of claim 1 wherein the time period is at least 6 months.

9. The method of claim 1 which further comprises administering an effective amount of fluorouracil.

10. A method of treating a human patient having metastatic renal cell carcinoma which comprises administering to such a patient about 4.5 micrograms/kg to about 9.0 micrograms/kg of pegylated interferon alpha-2b once a week for a time period sufficient to effect at least a partial tumor response.

11. The method of claim 10 wherein the time period is at least 6 months.

12. The method of claim 10 wherein the time period is at least 12 months.

13. The method of claim 10 wherein about 4.5 to about 6.5 micrograms/kg of pegylated interferon alpha-2b is administered once a week.

14. The method of claim 10 wherein a complete tumor response is effected.

15. The method of claim 10 which further comprises administering an effective amount of IL-2.

16. The method of claim 10 wherein the patient is a treatment-naive patient.

17. The method of claim 16 wherein the treatment-naive patient is one having newly diagnosed renal cell carcinoma.

18. The method of claim 16 wherein the patient is treatment-experienced patient.

19. The method of claim 18 wherein the treatment experienced patient is intolerant to interferon alpha or resistant to interferon alpha.

20. The method of claim 10 which further comprises administering an effective amount of fluorouracil.

* * * * *